US009303093B2

(12) United States Patent
Frangioni et al.

(10) Patent No.: US 9,303,093 B2
(45) Date of Patent: Apr. 5, 2016

(54) METHOD FOR PREPARING MICROCRYSTALLINE CELLULOSE

(75) Inventors: Giuseppe Frangioni, Sao Paulo (BR); Alexandre P. Frangioni, Sao Paulo (BR)

(73) Assignee: MARFIL COMERCIO E EMPREENDIMENTOS LTDA, Sao Paulo (BR)

( * ) Notice: Subject to any disclaimer, the term of this patent is extended or adjusted under 35 U.S.C. 154(b) by 0 days.

(21) Appl. No.: 13/261,008

(22) PCT Filed: May 3, 2010

(86) PCT No.: PCT/IB2010/001001
§ 371 (c)(1),
(2), (4) Date: Jan. 30, 2012

(87) PCT Pub. No.: WO2010/131088
PCT Pub. Date: Nov. 18, 2010

(65) Prior Publication Data
US 2012/0135505 A1 May 31, 2012

(30) Foreign Application Priority Data

May 14, 2009 (ES) .................................. 200901254

(51) Int. Cl.
C08B 15/02 (2006.01)
A61K 9/20 (2006.01)
A61K 47/38 (2006.01)
(52) U.S. Cl.
CPC ............... *C08B 15/02* (2013.01); *A61K 9/2054* (2013.01); *A61K 47/38* (2013.01)
(58) Field of Classification Search
CPC ....................................................... C08B 15/02
USPC ........................................... 536/127, 124, 56
See application file for complete search history.

(56) References Cited

U.S. PATENT DOCUMENTS

| | | | |
|---|---|---|---|
| 5,346,589 A | 9/1994 | Braunstein et al. | |
| 5,543,511 A | 8/1996 | Bergfeld et al. | |
| 6,392,034 B1 | 5/2002 | Trusovs | |
| 6,395,303 B1* | 5/2002 | Staniforth et al. | 424/499 |
| 6,810,812 B2* | 11/2004 | Fischer | 101/485 |
| 7,005,514 B2* | 2/2006 | Nguyen | 536/56 |
| 2010/0105891 A1* | 4/2010 | Nojiri et al. | 536/124 |

FOREIGN PATENT DOCUMENTS

| | | |
|---|---|---|
| WO | WO 97/32075 | 9/1997 |
| WO | WO 02/36875 | 5/2002 |
| WO | WO 02/057540 | 7/2002 |
| WO | WO 2004/011501 | 2/2004 |
| WO | WO 2008012346 A1 * | 1/2008 |

OTHER PUBLICATIONS

Bilba N. et al (RO 86547 A, Romania, Mar. 1985).*
International Search Report for PCT/IB2010/001001, mailed Aug. 25, 2010.

* cited by examiner

*Primary Examiner* — Scarlett Goon
*Assistant Examiner* — Everett White
(74) *Attorney, Agent, or Firm* — RatnerPrestia

(57) ABSTRACT

The present invention relates to a new method for preparing microcrystalline cellulose, comprising a prior step of compaction of the cellulose before degradation of the glucose chains and obtaining the suitable degree of polymerization. It is also described that the method of the invention allows a considerable reduction in the consumption of energy, water and possible chemicals which are used for reducing the degree of polymerization. The microcrystalline cellulose obtained can be used as a pharmaceutical excipient in tablets, and presents disintegration features comparable to those of the microcrystalline cellulose obtained by a spraying process.

11 Claims, 1 Drawing Sheet

METHOD FOR PREPARING MICROCRYSTALLINE CELLULOSE

This application is the U.S. national phase of International Application No. PCT/IB2010/001001, filed 3 May 2010, which designated the U.S., and claims priority to ES Application No. P 200901254, filed 14 May 2009, the entire content of each of which are hereby incorporated by reference.

TECHNICAL FIELD

The present invention relates to a new method for preparing microcrystalline cellulose.

PRIOR STATE OF THE ART

The cellulose is a natural polymer derived from D-glucose units, which are fused through $\beta(1\rightarrow4)$ glycosidic bonds, and which confer to it a linear structure. Many properties of cellulose depend on the chain length, i.e., on the number of glucose molecules forming the polymer. Said length is also known as the degree of polymerization, sometimes abbreviated as DP (Degree of Polymerization). The cellulose from wood pulp generally has a DP comprised between 300 and 1700; cotton and other plant fibers as well as celluloses of a bacterial origin have chain lengths comprised between 800 and 10000 units, which corresponds to a DP comprised between 800 and 10000.

Microcrystalline cellulose, also known as MCC, is a product obtained from cellulose, primarily consisting of crystalline aggregates. MCC is a purified, partially depolymerized cellulose which is presented as a white, odorless, flavorless powder made up of porous particles.

MCC is widely used as an excipient in pharmaceutical technology for tablet formulations due to its properties as a binder, disintegrant, diluent and lubricant.

MCC can also be applied in cosmetic products and in the food industry.

The first commercial forms of MCCs were described in 1961 in U.S. Pat. No. 2,978,446.

MCC is available on the market in different particle sizes and moisture content having different properties and applications as described in the book by R. C. Rowe et al., Handbook of Pharmaceutical Excipients, $4^{th}$ edition, Pharmaceutical Press, London, 2003 [ISBN: 0-85369-472-9].

Various methods for obtaining MCC from cellulose of different grades have been described in the state of the art. In all these methods, the cellulose chains are partially degraded, enzymatically or thermally, or by means of using chemical reagents. The amorphous portions of the cellulose, which are dissolved and removed, are hydrolyzed with these treatments.

One of the most used treatments consists of treating a purified cellulose material by means of hydrolytic degradation, generally in the presence of a strong mineral acid, such as hydrochloric acid for example.

A treatment with acid is described, for example, in U.S. Pat. No. 2,978,446, in which purified wood pulp containing amorphous and crystalline forms of cellulose, which is hydrolyzed with 2.5 N hydrochloric acid at a temperature of no less than 105° C., is used as starting material.

PCT patent application WO-A-99/15564 describes a method for obtaining MCC in which the cellulose is subjected to extrusion in contact with an acid solution. In the case of using purified cellulose, the process includes a single step of hydrolysis. If lignocellulosic material is used, it is necessary to apply a prior step of extrusion in alkaline medium to destroy the lignocellulosic complex and to thus obtain a purified cellulose.

Spanish patent ES-A-428908 describes several methods for obtaining MCC from purified cellulose with a high $\alpha$-cellulose content, including hydrolysis thereof at elevated temperatures (up to 160° C.) in the presence of hydrochloric acid or sulfuric acid.

At the end of the step of hydrolysis, the product is washed with abundant water to remove the acidic residues. This step of washing is important because, as described in the monograph corresponding to the microcrystalline cellulose in the *Encyclopedia of Polymer Science and Engineering*, John Wiley & Sons, 1985, New York, traces of inorganic impurities notably reduce the stability and life-time of some pharmaceutical active ingredients. Therefore a low inorganic residue content in the MCC offers a particular advantage in relation to producing tablets.

U.S. Pat. No. 5,769,934 describes a method for obtaining MCC in which pressurized steam at temperatures comprised between 180° C. and 350° C. is used. This method does not require using purified cellulose materials as starting material, but it does entail a certain risk due to the temperatures used.

PCT patent application WO-A-99/60027 also uses pressurized steam combined with a shear treatment to obtain MCC from a chemically produced cellulose pulp. Said method uses a prior purification process to recover the quality cellulose fibers.

PCT patent application WO-A-92/14760 describes a method for obtaining cellulose with a high degree of crystallinity by means of enzymatic hydrolysis that lasts between 24 and 48 hours. The raw material is $\alpha$-cellulose or a purified wood pulp referred to as "dissolving grade" pulp.

U.S. Pat. No. 6,392,034 describes a method for preparing MCC which comprises swelling a cellulose material with an alkaline solution, adding hydrogen peroxide to reduce the viscosity and separating the MCC from the suspension. The product obtained is treated with an acid solution to achieve a neutral reaction thereof.

U.S. Pat. No. 7,005,514 describes a method for obtaining MCC from paper grade cellulose pulp subjected to hydrolysis treatment in alkaline conditions, followed by hydrolysis in acid medium.

PCT patent application WO-A-02/057540 describes methods for obtaining MCC in which cellulose pulp that has not been subjected to a drying process is used as raw material.

PCT patent application WO-A-2004/011501 describes a method for obtaining MCC in which the cellulose material is subjected to high shear treatment at elevated temperature and in the presence of an active oxygen compound. Purified cellulose referred to as "dissolving grade" cellulose is generally used.

Therefore, there is a need to provide a method for preparing microcrystalline cellulose which does not have the drawbacks of the methods described in the state of the art, and particularly, in which easily readily available cellulose can be used as starting material; and which allows a reduction in the consumption of energy, water and chemicals.

OBJECT OF THE INVENTION

The inventors have discovered a new method for preparing microcrystalline cellulose from a less expensive and more readily available raw material. Said method allows reducing the consumption of energy, water and chemicals. The microcrystalline cellulose obtained furthermore has application features comparable to those of the microcrystalline cellulose obtained by a spraying process, which is more expensive.

The object of the invention is therefore a method for preparing microcrystalline cellulose.

DETAILED DESCRIPTION OF THE INVENTION

Figure 1:
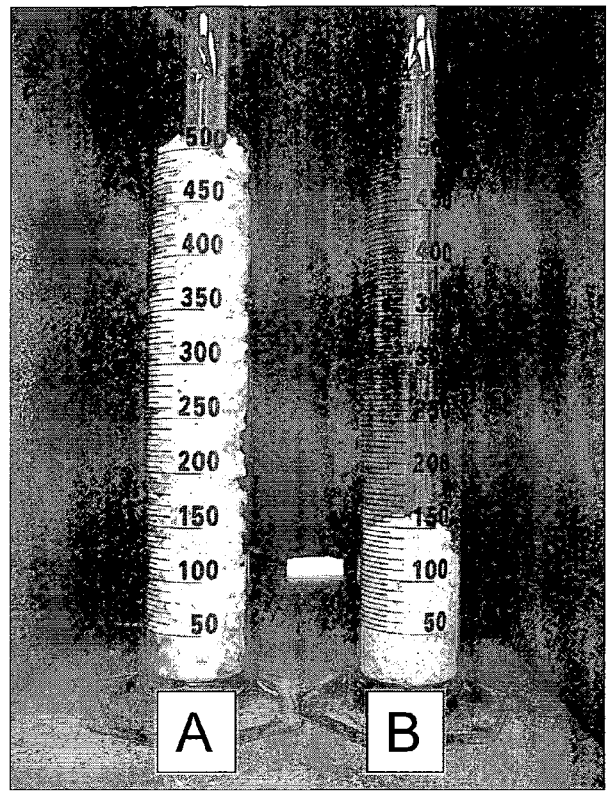
FIG. 1 shows the graduated cylinder (A) containing 35 g of ground "paper grade" cellulose, but without prior compaction. Said cellulose has an apparent density of approximately 0.06 g/ml. The graduated cylinder (B) also contains 35 g of compacted and ground "paper grade" cellulose, and has an apparent density of approximately 0.23 g/ml.

The method for preparing microcrystalline cellulose comprises:
1) compacting the substantially dry cellulose,
2) partially reducing the degree of polymerization of the compacted cellulose, and
3) isolating the microcrystalline cellulose obtained in step 2).

In the method of the invention, the key step is the compaction of the substantially dry cellulose which takes place before the partial reduction of the degree of polymerization thereof.

The Cellulose

The raw material which is used in the method of the invention is substantially dry cellulose.

Said cellulose is obtained by drying a suspension of cellulose fibers in water, which is referred to as cellulose pulp or cellulose paste. The substantially dry cellulose has a water content generally comprised between 7% and 11%

Several types of wood can be used for obtaining cellulose pulp, and are known as pulwood, which include soft wood such as spruce, pine, fir and larch, and hard wood such as eucalyptus, birch, maple, and locust.

The production of cellulose generally comprises the following steps:
1) Removing the bark from the wood,
2) Producing chips by means of using special mills, and
3) Separating the cellulose fibers holding the wood together from the remaining components of the wood.

The separation of the fibers can be performed in different ways, and according to the process used the pulps are referred to as mechanical, thermomechanical or chemical pulps.

The combination of the species of wood used, the production processes and the bleaching and purification phases, mean that the cellulose is available on the market in different grades and formats.

Therefore, two large groups of cellulose are distinguished on the market: "paper grade" and "dissolving grade".

"Paper grade" cellulose is a cellulose which is used for producing paper and is abundantly available on the market, for example the product JARILIPTUS, marketed by the company Jari Celulose.

"Paper grade" cellulose can come from types of wood which can have short or long fibers. For example, the cellulose obtained from eucalyptus wood (short fiber) has a degree of polymerization of approximately 1150, and the cellulose obtained from pine wood (long fiber) has a degree of polymerization of approximately 1300.

"Dissolving grade" cellulose is a purified cellulose intended for producing cellulose derivatives such as rayon or cellulose acetate for example. The production thereof is more limited and more expensive due to the purity which characterizes it. It is available on the market as TEMALFA 93 product marketed by the company Tembec, for example.

The method of the invention is suitable for preparing microcrystalline cellulose with a low degree of polymerization and with good disintegrating characteristics from "paper grade" cellulose, which is a readily available raw material. The greatest advantages of the method of the invention are achieved by using said raw material.

Nevertheless, more purified celluloses can also be used in said method as a single raw material or mixed with "paper grade" cellulose. One of the most typical purified celluloses is "dissolving grade" cellulose.

Therefore, the cellulose which is used in the method of the invention is selected from the group consisting of: "paper grade" cellulose, "dissolving grade" cellulose, and/or mixtures thereof; "paper grade" cellulose, "dissolving grade" cellulose, and/or mixtures thereof are preferably used; a mixture of "paper grade" cellulose and "dissolving grade" cellulose is more preferably used.

When a mixture of "paper grade" cellulose and "dissolving grade" cellulose is used, any ratio between the two raw materials can be used. The method of the invention is suitable for using a ratio comprised between 100:0 to 0:100, a mixture of "paper grade" cellulose and "dissolving grade" cellulose is preferably used comprised between 90:10 and 100:0, more preferably between 95:5 and 99:1, and even more preferably 100% "paper grade" cellulose is used.

Dry cellulose can be presented in rolls or in sheets. The sheets are obtained from rolls that were unwound, cut and baled. The generally have a grammage comprised between 750 and 1200 g/m². The grammage indicates the weight in grams per square meter of the roll or of the sheet, and depends on the type of pulp, on the drying process and on the final destination of the cellulose.

It is preferable to use rolls of cellulose in the method of the invention because it facilitates continuous work.

Compaction of the Cellulose

The step of compaction in the method of the invention is performed on the substantially dry cellulose before performing the partial reduction of its degree of polymerization.

The compaction of the cellulose can be performed, for example, by passing the sheet of cellulose between the rollers of a conventional rolling mill such as those typically used in metallurgy.

Rolling mills are machines for shaping metallurgical products and for compacting cellulose in this case by the pressure exerted by two rotating cylinders between which the metal and the cellulose undergo thickness reduction and proportional elongation.

Cylinder rolling mills generally consist of two, three or four cylinders assembled horizontally one above the other on a robust vertical frame called stand. The gaps between the cylinders for the passage of the metal or of the cellulose are adjustable. Rolling mills with three or four cylinders usually work the metal or the cellulose successively between the lower cylinders and then between the upper cylinders. Some rolling mill stands with two cylinders can have supplementary cylinders with a larger diameter placed on either side of the working cylinders.

The roller milling machine typically includes rotating cylinders the diameter of which can vary considerably and can be comprised between 115 and 430 mm, and the width can be comprised between 130 and 430 mm.

A rolling mill with two cylinders is preferably used in the method of the invention.

Rolling mills suitable for carrying out the method of the invention can be found on the market, such as the LA-6 model marketed by the company Guttmann (São Paulo, Brazil), for example.

Upon passing through the rolling mill, the sheet of cellulose is subjected to a low compaction force comprised between 245 N and 400 N, with torques comprised between 6560 and 9200 Nm.

The method of the invention typically includes a step of grinding the compacted cellulose before performing the partial reduction of the degree of polymerization thereof.

Said grinding can be carried out by means of a knife mill for example, which is suitable for grinding materials of medium hardness to soft materials, such as plastics, including fibrous materials such as cellulose.

The mills include perforated cloths with circular openings with a diameter comprised between 6 and 20 mm.

Knife mills can be found on the market marketed by the companies Rone Moinhos (Carapicuiba, Brazil) or Laval Lab (Laval, Canada), for example.

Compacted cellulose is usually ground to a mean size comprised between 2 mm and 20 mm, for example a mean size of 2 mm or of 10 mm.

The compacted cellulose fragments present an apparent density greater than that of the non-compacted cellulose fragments, which is generally comprised between 0.04 and 0.06 g/ml.

The compacted cellulose fragments typically have an apparent density comprised between 0.10 and 0.25 g/ml, preferably between 0.15 and 0.25 g/ml, and even more preferably between 0.20 and 0.25 g/ml.

FIG. 1 shows the graduated cylinder (A) containing 35 g of ground "paper grade" cellulose, but without prior compaction. Said cellulose has an apparent density of approximately 0.06 g/ml. The graduated cylinder (B) also contains 35 g of compacted and ground "paper grade" cellulose, and presents an apparent density of approximately 0.23 g/ml.

Figure 2:
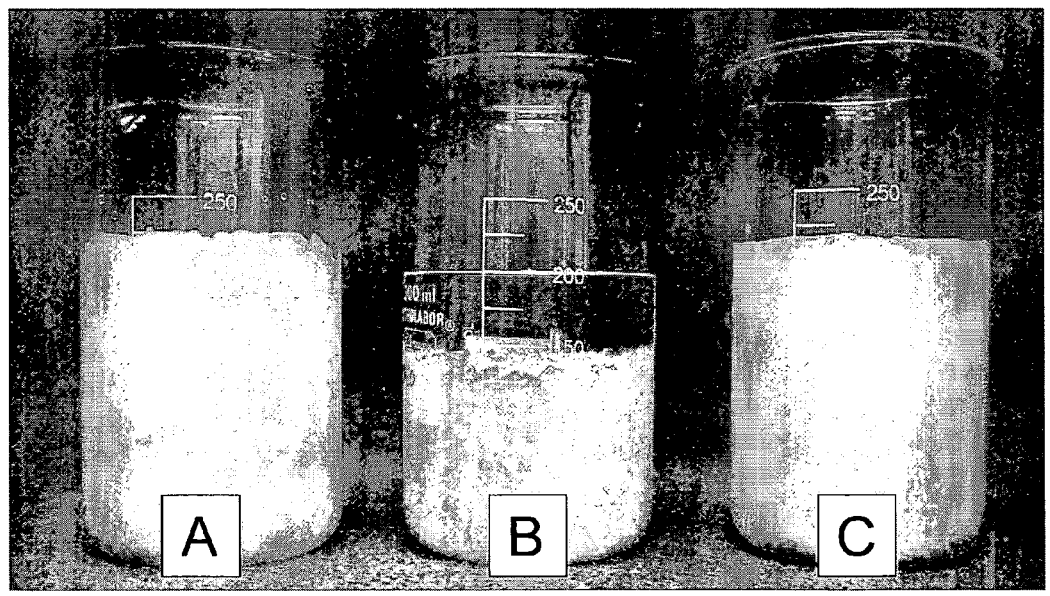
FIG. 2 shows the beaker (A) containing a suspension in water of ground "paper grade" cellulose, but without prior compaction, at a concentration of 9.8% by weight/volume. The beaker (B) also contains an aqueous suspension at 9.8% by weight/volume of compacted and ground "paper grade" cellulose. In the beaker (C) there is an aqueous suspension of compacted and ground "paper grade" cellulose with a concentration of 21.8% expressed by weight/volume. It can be observed that the aqueous suspension of the beaker (C) contains more than twice the solids as the suspension of beaker (A), so when using compacted and ground cellulose, the microcrystalline cellulose production capacity can be increased.

It can be observed in FIG. 2 that a suspension in water of ground "paper grade" cellulose, but without prior compaction, at a concentration of 9.8% by weight/volume (beaker A), occupies the same volume as an aqueous suspension of compacted and ground "paper grade" cellulose with a concentration of 21.8% expressed by weight/volume (beaker C), i.e., the aqueous suspension of beaker (C) contains more than twice the solids as the suspension of beaker (A). Therefore, the microcrystalline cellulose production capacity can be increased for a specific industrial facility when using compacted cellulose according to the method of the invention.

Partial Reduction of the Degree of Polymerization of the Cellulose and Isolation of the Microcrystalline Cellulose The degree of polymerization is a parameter which indicates the number of glucose units forming the cellulose chains. It can be determined from the viscosity of a solution of the cellulose in a cuprammonium solution, as described in the article by O. A. Battista, Ind. Eng. Chem., 1950, 42 (3), 502-507.

The microcrystalline cellulose that is obtained with the method of the invention presents a partial reduction of the degree of polymerization of the starting cellulose, and is generally comprised between 220 and 340. Accordingly, the microcrystalline cellulose obtained according to the method of the invention presents a degree of polymerization less than that of the starting cellulose.

The partial reduction of the degree of polymerization of compacted cellulose can be carried out by means of different methods well known by the person skilled in the art, such as degradation in acid medium, degradation by pressurized steam at elevated temperatures, enzymatic degradation, degradation with an oxidizing agent in alkaline medium, or degradation in alkaline medium followed by hydrolysis in acid medium.

A method for partially reducing the degree of polymerization of the cellulose including degradation in acid medium is described, for example, in U.S. Pat. No. 2,978,446, or in PCT patent application WO-A-99/15564.

The use of degradation by pressurized steam at elevated temperatures comprised between 180° C. and 350° C. is described, for example, in U.S. Pat. No. 5,769,934, or in PCT patent application WO-A-99/60027.

The use of enzymatic degradation for reducing the length of cellulose chains is described, for example, in PCT patent application WO-A-92/14760.

An example of degradation with oxidizing agent in alkaline medium can be found, for example, in U.S. Pat. No. 6,392,034.

A method which includes degradation in alkaline medium followed by hydrolysis in acid medium is described, for example, in U.S. Pat. No. 7,005,514.

Degradation in acid medium is preferably used in the method of the invention.

The acids which can be used include strong mineral acids such as hydrochloric acid, sulfuric acid, and phosphoric acid; hydrochloric acid is preferably used.

In the method of the invention, once the partial reduction in the degree of polymerization of the cellulose has occurred, the microcrystalline cellulose obtained is isolated.

To that end, the method of the invention for obtaining microcrystalline cellulose includes additional steps which lead to the isolation of the product. These steps can possibly include neutralization in the case of having used acid or alkaline medium for hydrolyzing the cellulose, filtration of the suspension containing the microcrystalline cellulose, purification by means of washing operations with purified water, drying, grinding and granulometric classification according to particle size.

The removal of the impurities in the microcrystalline cellulose after the process for reducing the degree of polymerization allows obtaining a product which is compatible with most pharmaceutical active ingredients. It is known that the presence of inorganic impurities in microcrystalline cellulose considerably reduces the stability of some of said active ingredients.

A typical process for carrying out the partial reduction of the degree of polymerization of the compacted cellulose in acid medium comprises loading demineralized water in a stainless steel reactor prepared to withstand the pressure of steam heated to 140° C. and heating it to a temperature comprised between 88° C. and 92° C. The mineral acid, for example hydrochloric acid concentrated at 33% by weight, and the compacted and ground cellulose are added under stirring.

The concentration of the cellulose in the water is generally comprised between 16.6% and 23.3% expressed by weight/volume, preferably between 20.0% and 22.0%; the concentration expressed by weight/weight is comprised between 14.2% and 18.9%, preferably between 16.7% and 18.2%, and the molarity of the hydrochloric acid is typically comprised between 0.0052 and 0.0130 M, preferably between 0.0052 and 0.0085 M.

The reactor is then closed and the suspension is heated up to a temperature comprised between 90° C. and 160° C., preferably between 130° C. and 140° C.

The suspension of cellulose is maintained under stirring at said temperature for a period generally comprised between 2 and 5 hours, preferably between 2.5 and 3.5 h.

Once the period of acid hydrolysis of the cellulose had ended, the microcrystalline cellulose obtained is isolated. To that end the reactor is cooled and degassed until reaching atmospheric pressure.

When the temperature of the suspension is between 85° C. and 100° C., preferably between 90° C. and 100° C., the residual acid is neutralized with a alkaline compound, for example sodium carbonate, until the pH is at a value generally comprised between 5.5 and 7.0.

To isolate the microcrystalline cellulose, the neutralized suspension can be filtered under vacuum at a temperature generally comprised between 70° C. and 95° C., preferably between 85° C. and 90° C.

The microcrystalline cellulose cake which is obtained is washed with demineralized water to remove the residues of the salts formed during neutralization until obtaining a conductivity of the effluents which is typically equal to or less than 300 μS.

The wet microcrystalline cellulose cake substantially free of salts can be dried in a fluid bed dryer at a temperature of approximately 65° C. until reaching a moisture content generally comprised between 2.0% and 6.0%. The production yield of microcrystalline cellulose is typically comprised between 82% and 84%.

Finally, the microcrystalline cellulose can be ground and granulometrically classified according to particle size.

The degree of polymerization of the microcrystalline cellulose which is obtained with the method of the invention is generally comprised between 220 and 340.

The total consumption of demineralized water corresponding to the step of hydrolysis and to purification is generally comprised between 18 and 27 l of water per kg of microcrystalline cellulose, even typically between 19 and 23 l of water per kg of microcrystalline cellulose.

The consumption of heat is generally estimated to be comprised between 2500 and 3000 kWh per kg of microcrystalline cellulose, even typically between 2500 and 2750 kWh per kg of microcrystalline cellulose.

The method of the invention for obtaining microcrystalline cellulose presents advantages with respect to a method which does not include the prior step of compaction of the cellulose.

For example, in the case of carrying out a partial reduction of the degree of polymerization in the presence of hydrochloric acid in an industrial reactor with a volume of 9000 l of water, the differences between a method using compacted cellulose as raw material, and a method using non-compacted cellulose is presented in Table I:

TABLE I

| Parameter | Units | Process with non-compacted cellulose | Process with compacted cellulose |
| --- | --- | --- | --- |
| Apparent density | kg/m³ | 40-60 | 200-250 |
| Weight of cellulose | kg | 920 | 1800-2000 |
| Concentration of cellulose in water | % (W/V) | 10.2 | 20.0-22.2 |
| Concentration of cellulose in the suspension | % (W/W) | 9.3 | 16.7-18.2 |
| Weight of hydrochloric acid (100%) | kg | 4.3 | 1.7-2.8 |
| Weight of hydrochloric acid (100%) to the weight of cellulose | kg HCl/kg cellulose | 0.0046 | 0.00085-0.0016 |
| Weight of sodium carbonate | kg | 6.24 | 2.46-4.06 |
| Weight of sodium chloride formed | kg | 6.89 | 2.72-4.49 |
| Weight of carbon dioxide formed | kg | 2.59 | 1.02-1.69 |
| Consumption of water in the hydrolysis and in the purification | l water/kg MCC | 29-33 | 18-23 |
| Consumption of water in drying | l water/kg MCC | 1.6-2.2 | 0.8-1.2 |
| Consumption of energy | kCal/kg MCC | 4500-5500 | 2500-3000 |

It can be observed that the method for preparing microcrystalline cellulose in which compacted cellulose is used before performing the hydrolysis thereof presents lower consumptions of energy, water, and chemicals per kg of microcrystalline cellulose obtained in comparison with the methods in which non-compacted cellulose is used.

Furthermore, it has been found that a greater reduction of the degree of polymerization is achieved if compacted cellulose is used. Table II presents the degrees of polymerization (DP) reached at different times during hydrolysis in acid medium at laboratory scale of a compacted cellulose and of a non-compacted cellulose, and also the degree of polymerization obtained in relation to the initial value in percentage form:

TABLE II

| Time | Compacted cellulose (DP) | % | Non-compacted cellulose (DP) | % |
| --- | --- | --- | --- | --- |
| Initial | 1236 | 100 | 1458 | 100 |
| 1 hour | 284 | 22.9 | 417 | 28.6 |
| 2 hours | 279 | 22.5 | 397 | 27.2 |
| 3 hours | 248 | 20.1 | 392 | 26.9 |

It can be observed that the compaction of cellulose causes a complementary reduction of the degree of polymerization of the cellulose: it goes from 1458 to 1236, which entails a reduction of approximately 15%. It can also be observed that in the hydrolysis conditions, the degree of polymerization of the cellulose which has been previously compacted is reduced at a higher speed than in the event that the cellulose has not been compacted.

It is observed at the same time that compaction allows obtaining degree of polymerization values which mean that the microcrystalline cellulose obtained from compacted cellulose has disintegrating properties similar to those of microcrystalline cellulose obtained by spraying, having a method for obtaining them with a higher energy cost.

Said results are described in Example 4 located at the end of this description. Said example describes disintegration tests for placebo tablets produced from different batches of microcrystalline cellulose obtained according to the method of the invention, microcrystalline cellulose obtained from non-compacted cellulose, and from the commercial product AVICEL PH-102 obtained by spraying.

It has surprisingly been observed that including a step of compaction of the cellulose before performing the reduction of the degree of polymerization thereof achieves:
- increasing the concentration of solids in the reactor,
- reducing the consumption of energy,
- reducing the consumption of water necessary for purifying the microcrystalline cellulose,
- reducing the consumption of chemicals,
- using "paper grade" cellulose, a less expensive and more readily available raw material, for preparing microcrystalline cellulose, and
- obtaining a microcrystalline cellulose with disintegrating properties comparable to those of a microcrystalline cellulose obtained by spraying, a process involving a greater consumption of energy.

The following examples serve to illustrate but not limit the invention.

EXAMPLES

Comparative Example

Preparing Microcrystalline Cellulose without the Prior Step of Compaction 16 liters of demineralized water were loaded in a reactor and heated at a temperature comprised between 88° C. and 92° C.

Between 23.1 g of 33% hydrochloric acid by weight and 1635 g of "paper grade" cellulose were added under stirring. Next the reactor was closed and the suspension was heated to a temperature comprised between 130° C. and 140° C.

The suspension of cellulose was maintained under stirring at said temperature for a period comprised between 1 h 40 min and 2 h 20 min.

Once the period of acid hydrolysis of the cellulose had ended, the reactor was cooled and degassed until reaching atmospheric pressure.

When the temperature reached 95° C., 11.1 g of sodium carbonate were added to adjust the pH to a value comprised between 5.5 and 7.0.

The neutralized suspension was filtered under vacuum at a temperature comprised between 70° C. and 95° C. The microcrystalline cellulose cake was washed with demineralized water to remove the sodium chloride formed in the neutralization until the conductivity of the effluents was equal to or less than 300 μS.

The wet microcrystalline cellulose cake substantially free of salts was dried in a fluid bed dryer at a temperature of 65° C. until reaching a moisture content comprised between 2.0% and 6.0%. 1206 g of microcrystalline cellulose were obtained.

The microcrystalline cellulose was then ground and granulometrically classified according to particle size.

The microcrystalline cellulose obtained presented a degree of polymerization of 325.

The total consumption of demineralized water corresponding to the step of hydrolysis and to purification was comprised between 29 and 33 l of water per kg of microcrystalline cellulose.

The consumption of energy was estimated to be comprised between 4500 and 5500 kcal per kg of microcrystalline cellulose.

Example 1

Producing Compacted and Ground Cellulose

Strips of "paper grade" cellulose with a thickness comprised between 2.10 and 2.25 mm, a length comprised between 80 and 100 cm and a width comprised between 10 and 15 cm, were used. The grammage of said cellulose was comprised between 730 and 780 $g/m^2$.

Said strips of cellulose were introduced between the rotating cylinders of a LA-6 model rolling mill of the company Guttman (São Paulo, Brazil) and were subjected to compaction under a force comprised between 245 N and 400 N, with torques comprised between 6560 and 9200 Nm.

The compacted strips of cellulose were ground in an FB-5530 model rotating knife mill of the company Rone Moinhos (Carapicuiba, Brazil), which included perforated cloths with circular openings that had a diameter comprised between 6 and 20 mm.

Compacted and ground cellulose, which is suitable for being subjected to a process for reducing the degree of polymerization thereof, was obtained.

The apparent density of the compacted and ground cellulose was 0.23 g/ml, whereas the apparent density of the non-compacted and ground cellulose was 0.07 g/ml.

Example 2

Producing Microcrystalline Cellulose 16 liters of demineralized water were loaded in a reactor and heated at a temperature comprised between 88° C. and 92° C.

8.5 g of 33% hydrochloric acid by weight and 3555 g of compacted and ground cellulose obtained in Example 1 were added under stirring. Next the reactor was closed and the suspension was heated to a temperature comprised between 130° C. and 140° C.

The suspension of cellulose was maintained under stirring at said temperature for a period comprised between 2.5 and 3.5 hours.

Once the period of acid hydrolysis of the cellulose had ended, the reactor was cooled and degassed until reaching atmospheric pressure.

When the temperature reached 95° C., 4.0 g of sodium carbonate were added to adjust the pH to a value comprised between 5.5 and 7.0.

The neutralized suspension was filtered under vacuum at a temperature comprised between 70° C. and 95° C. The microcrystalline cellulose cake was washed with demineralized water to remove the sodium chloride formed in the neutralization until the conductivity of the effluents was equal to or less than 300 μS.

The wet microcrystalline cellulose cake substantially free of salts was dried in a fluid bed dryer at a temperature of 65° C. until reaching a moisture content comprised between 2.0% and 6.0%. 2590 g of microcrystalline cellulose were obtained.

The microcrystalline cellulose was then ground and granulometrically classified according to particle size.

The degree of polymerization of the microcrystalline cellulose that was obtained was comprised between 220 and 340.

The total consumption of demineralized water corresponding to the step of hydrolysis and to purification was comprised between 18 and 27 l of water per kg of microcrystalline cellulose.

The consumption of water during the step of drying was comprised between 0.8 and 1.6 l of water per kg of microcrystalline cellulose.

The consumption of energy was estimated to be comprised between 2500 and 3000 kcal per kg of microcrystalline cellulose.

Example 3

Hydrolysis Test in Acid Medium at Laboratory Scale 3190 ml of demineralized water were loaded in a laboratory round-bottom flask and heated at a temperature comprised between 88° C. and 92° C.

Between 70.2 g of 33% hydrochloric acid by weight and 100 g of compacted and ground cellulose obtained in Example 1 were added under stirring. Next the suspension was heated to a temperature comprised between 98° C. and 101° C., i.e., under reflux.

The suspension of cellulose was maintained under stirring at said temperature for a period comprising 3 hours.

Once the period of acid hydrolysis of the cellulose had ended, the round-bottom flask was cooled.

When the temperature reached 90° C., 32.0 g of sodium carbonate were added to adjust the pH to a value comprised between 5.5 and 7.0.

The neutralized suspension was filtered under vacuum at a temperature comprised between 70° C. and 95° C. The microcrystalline cellulose cake was washed with demineralized water to remove the sodium chloride formed in the neutralization until the conductivity of the effluents was equal to or less than 300 μS.

The wet microcrystalline cellulose cake substantially free of salts was dried in a fluid bed dryer at a temperature of 65° C. until reaching a moisture content comprised between 2.0% and 6.0%. 70 g of microcrystalline cellulose were obtained.

The microcrystalline cellulose was then ground and granulometrically classified according to particle size.

The degree of polymerization of the microcrystalline cellulose that was obtained is described in Table II.

Example 4

Producing Placebo Tablets

Placebo tablets were produced using different batches of microcrystalline cellulose obtained according to the process described in Example 2 as disintegrant. Batches 1 and 2 consisted of microcrystalline cellulose obtained from "paper grade" cellulose compacted and ground to a size of 2 mm, whereas in the case of batch 3, the cellulose was ground to a size of 10 mm. Tablets were also produced from microcrystalline cellulose obtained without prior compaction of the cellulose (Comparative Example) and using the commercial product AVICEL PH-102 of the company FMC Biopolymer, which is obtained by spraying.

The tablets having microcrystalline cellulose as a single component were produced in a LAWES 2000 tablet compressing machine of the company Lawes (Brazil). The tablets presented a mean weight of 450 mg and were compressed to two hardnesses: 107.8 N (equivalent to 11 kp) and a 294 N (equivalent to 30 kp) with a 12 mm punch.

Table III presents the disintegration times determined from the tablets produced in this example:

TABLE III

| Microcrystalline cellulose | Degree of polymerization | Disintegration time 107.8N | Disintegration time 294N |
| --- | --- | --- | --- |
| Example 2, Batch 1 | 191 | 42 s | 5 min 14 s |
| Example 2, Batch 2 | 199 | 29 s | 3 min 8 s |
| Example 2, Batch 3 | 220 | 36 s | 4 min 10 s |
| Comparative Example | 325 | 13 min 10 s | >2 h |
| AVICEL PH-102 | 237 | 35 s | 6 min 8 s |

The disintegration of the tablets was determined in a standard disintegration apparatus according to the process described in the US Pharmacopoeia, in which six randomly selected tablets and 750 ml of water at a temperature of 37±2° C. were used. The disintegration time shown in Table III expresses the disintegration time of the last tablet in each test.

Tablet hardness was determined in a durometer of the company VanKel, and the result expresses the mean hardness of ten randomly selected tablets.

It can be observed that the microcrystalline cellulose produced according to the method of the invention presents a degree of polymerization less than that of the microcrystalline cellulose produced from cellulose that has not been compacted previously.

It can also be observed that the disintegration time determined for the tablets produced with microcrystalline cellulose produced according to the method of the invention is comparable to disintegration time determined for the tablets produced with commercial microcrystalline cellulose obtained by spraying.

The invention claimed is:

1. A method for preparing microcrystalline cellulose, wherein the method comprises:
    1) compacting a substantially dry cellulose, wherein the compacting provides a compacted cellulose which, when ground to a mean size comprised between 2 mm and 20 mm, presents an apparent density comprised between 0.10 and 0.25 g/ml,
    2) partially reducing the degree of polymerization of the compacted cellulose, and
    3) isolating the microcrystalline cellulose obtained in step 2.

2. The method according to claim 1, wherein the cellulose is selected from the group consisting of: "paper grade" cellulose, "dissolving grade" cellulose, and/or mixtures thereof.

3. The method according to claim 2, wherein a mixture of "paper grade" cellulose and "dissolving grade" cellulose is used.

4. The method according to claim 3, wherein a mixture of "paper grade" cellulose and "dissolving grade" cellulose is used wherein the ratio between "paper grade" cellulose and "dissolving grade" cellulose is comprised between 90:10 and 100:0.

5. The method according to claim 1, wherein a rolling mill having two cylinders is used in the compaction.

6. The method according to claim 1, wherein the partial reduction of the degree of polymerization of the cellulose is carried out by means of a process selected from the group consisting of: degradation in acid medium, degradation by pressurized steam at elevated temperatures, enzymatic degradation, degradation with an oxidizing agent in alkaline medium, or degradation in alkaline medium followed by hydrolysis in acid medium.

7. The method according to claim 6, wherein the partial reduction of the degree of polymerization of the cellulose is carried out by means of degradation in acid medium.

8. The method according to claim 7, wherein the acid medium is generated by an acid selected from the group consisting of hydrochloric acid, sulfuric acid, and phosphoric acid.

9. The method according to claim 8, wherein hydrochloric acid is used.

10. The method according to claim 1, wherein it includes as additional steps for isolating the microcrystalline cellulose neutralization in the case of having used acid or alkaline medium for hydrolyzing the cellulose, filtration of the suspension containing the microcrystalline cellulose, purification by means of washing operations with purified water, drying, grinding and granulometric classification according to particle size.

11. The method of claim 1, wherein during the compacting a sheet of cellulose is passed through a rolling mill and subjected to a compaction force between 245 N and 400 N, with a torque of between 6560 and 9200 Nm.

\* \* \* \* \*